United States Patent [19]
Heath et al.

[11] Patent Number: 6,015,888
[45] Date of Patent: Jan. 18, 2000

[54] ALLELE OF HUMAN HISTAMINE $H_2$ RECEPTOR AND METHODS OF DETECTION OF $H_2$ RECEPTOR VARIANTS

[75] Inventors: Paul Roy Heath, Sheffield; Paul Richard Orange, Preston; Ronald Carl Alan Pearson, Newcastle-upon-Tyne; Simon Ralph Wright, Sheffield, all of United Kingdom

[73] Assignee: University of Sheffield, United Kingdom

[21] Appl. No.: 08/875,540

[22] PCT Filed: Jan. 30, 1996

[86] PCT No.: PCT/EP96/00397

§ 371 Date: Jan. 5, 1998

§ 102(e) Date: Jan. 5, 1998

[87] PCT Pub. No.: WO96/23880

PCT Pub. Date: Aug. 8, 1996

[30] Foreign Application Priority Data

Jan. 30, 1995 [GB] United Kingdom .................. 9503866

[51] Int. Cl.$^7$ .......................... C07H 21/04; C12N 15/12; C12N 15/63
[52] U.S. Cl. ...................... 536/23.5; 536/23.1; 536/24.5; 435/69.1; 435/320.1; 435/325; 435/252.3
[58] Field of Search .................................. 536/23.5, 23.1, 536/24.5; 435/69.1, 320.1, 325, 252.3

[56] References Cited

FOREIGN PATENT DOCUMENTS

| | | |
|---|---|---|
| 2 297 328 | 7/1996 | United Kingdom . |
| 2 312 211 | 10/1997 | United Kingdom . |
| WO 96/23880 | 8/1996 | WIPO . |
| PCT/EP96/00397 | 7/1997 | WIPO . |

OTHER PUBLICATIONS

Gantz, et al. "Molecular Cloning of the Human Histamine H2 Receptor" Biochemical and Biophysical Research Communications vol. 178, No. 3, 1991. pp. 1386–1392.

Gantz, et al. "Molecular Basis for the Interaction of Histamine with the Histamine H2 Receptor" The Journal of Biological Chemistry 1992 vol. 267 No. 29, Issue of Oct. 15, pp. 10840–10843.

Nishi, et al. "Identification of the Promoter Region of The Human Histamine $H_2$–Receptor Gene" Biochemical and Biophysical vol. 320 1995 pp. 1096–1101.

Ohta, et al. "Site–Directed Mutagenesis of the Histamine $H_1$ Receptor: Roles Of Aspartic Acid$^{107}$, Asparagine$^{194}$ and Threonine$^{198}$" vol. 203, No. 2.1994.

Orange, et al. "Allelic variation of the human histamine $H_2$ receptor gene is a major predisposing factor for schizophrenia".

Orange, et al. "Individuals with schizophrenia have an increased incidence of the $H_2R_{649G}$ allele for the histamine $H_2$ receptor gene" Molecular Phychiatry 1996 466–469.

Orange, et al. "Allelic Variations of the human histamine $H_2$ receptor gene", Molecular Neuroscience, NeuroReport 7:1293–1296 (1996).

Lin et al. Diffrential Fluorescent Staining of Human Chromosomes with Daunomycin and Adriamycin—The D–Bands Science, vol. 190, pp. 61–63, 1975.

*Primary Examiner*—Elizabeth Kemmerer
*Assistant Examiner*—Nirmal S. Basi
*Attorney, Agent, or Firm*—Fish & Richardson P.C.

[57] ABSTRACT

The invention relates to allelic variants of human histamine $H_2$ receptor genes and primer sequences useful in detecting such genes.

8 Claims, 1 Drawing Sheet

ALLELE OF HUMAN HISTAMINE H₂ RECEPTOR AND METHODS OF DETECTION OF H₂ RECEPTOR VARIANTS

This is a 371 of International Patent Application No. PCT/EP96/00397, with an international filing date of Jan. 30, 1996, now pending, which claims priority from United Kingdom Patent Application No. 9503866.7 with a filing date of Jan. 30, 1995.

TECHNICAL FIELD

This invention relates to the detection of variations in human histamine $H_2$ receptors, and more particularly to the development of new compounds useful in the sequencing and identification of a human histamine $H_2$ receptor and their use in the diagnosis and treatment of certain human disorders, for example, brain disorders. The invention also relates to new compounds and a method for detecting an allelic polymorphic variation within the human population for the gene encoding the histamine $H_2$ receptor and their use in the diagnosis and treatment of human disorders.

BACKGROUND ART

The human $H_2$ receptor was first identified by Black et al Nature (1972), 236, 385–390. This was followed by the demonstration of the receptor in the mammalian brain by Baudry et al (1975) Nature 253, 362–363, and Haas and Bucher (1975) Nature 255, 634–635. Gantz et al (1991) Biochem. Biophys. Res. Comm. 178,3, 1386–1392 have recently identified the sequence of a human $H_2$ receptor cDNA from gastric parietal cells by using the polymerase chain reaction (PCR) and degenerated oligonucleotide primers whose sequence was obtained from the canine $H_2$ receptor previously cloned by this group, Gantz et al (1991) Proc. Nat. Acad. Sci. USA 88, 429–433. This sequence was characterised as an intronless gene encoding a typical seven transmembrane domain aminergic receptor protein.

The receptor is coupled to heterotrimeric GTPases (G proteins), but differs from other monoamine receptors in this G protein coupled superfamily in several respects. The human gastric $H_2$ receptor is shorter than most other receptors in this class (359 amino acids) and lacks the two serine residues in the fifth transmembrane region (TM5). There exists instead an aspartate and a threonine residue, so far unique in this region. These two residues may be important for binding with the nitrogen atoms of the imidazole ring of histamine as suggested by Birdsall (1991) Trends in Pharmacological Sci. Jan, 12, 9–10.

Histamine is a natural constituent of many organs and tissues including the gastrointestinal tract, the immune system and the brain, Green et al (1987) Agents and Actions 22, 1–15. It is a central neurotransmitter in the brain and is formed in the posterior hypothalamus from exogenous histidine by histidine decarboxylase (HDC). It is subsequently metabolised by histamine methyltransferase (HMT), Prell et al (1986) Ann. Rev. Neurosci. 9, 209–254. The cell bodies and neuronal pathways for histamine have been mapped in the human brain using immunocytochemistry by Panula et al (1990) Neuroscience 34, 127–132. Its cells project from the tuberomamillary nucleus of the posterior hypothalamus to almost every region of the brain. There are three known histamine receptors; $H_1$, $H_2$ and $H_3$, the latter functioning as an autoreceptor. The $H_2$ receptor specifically has been localised in the human brain by Traiffort et al (1992) J. of Neurochem. 59, 1, 290–299. using receptor autoradiography.

Histamine is known to have significant effects in the central nervous system (CNS). It has been implicated in the CNS mediated mechanisms of arousal ever since the sedating effect of $H_1$ receptor antagonists (eg,. chlorpheniramine, chloropromazine) had been noticed clinically. The use of $H_2$ receptor antagonists in the human brain however, has shown, that these compounds, unlike those acting on the $H_1$ receptor, do not produce any effect on psychomotor functioning, or a subjective feeling of sedation or arousal in healthy subjects, White et al (1988) Psychopharmacology 95, 1–14. Some $H_2$ receptor antagonists (eg. cimetidine) are known to cause confusion in elderly or severely medically ill patients, perhaps in part due to a co-existing anti-cholinergic effect. $H_1$ and $H_2$ receptor antagonists in large doses have been reported to cause hallucinations, Csillag et al (1973) Med. J. Aust. 1, 653–654, Argawal (1978) J. Am. Med. Assoc. 240, 214. Animal studies have shown that histamine applied directly to the hippocampus, where there is the highest level of activity of the $H_2$ receptor, will induce psychomotor withdrawal and decreased exploratory behaviour. The above evidence has led to the conclusion that $H_1$ receptor systems are excitatory in the terms of arousal and motivated behaviour whilst $H_2$ receptor systems are inhibitory in this respect, Alvarez and Banzan (1985) Physiol. and Beh. 34, 661–664 and (1986) Physiol. and Beh. 37, 39–45, White et al (1988) supra.

The $H_2$ receptor is a site of action of various compounds used in the treatment of psychiatric disorders eg. amitriptyline and mianserin, Traiffort et al (1992) supra. Kaminsky et al (1990) The Lancet 335, 1351–1352 and (1991) Schizophrenia Bull. 4, 318–319 have reported the successful response of patients with chronic, predominantly negative type schizophrenia, to the highly specific $H_2$ receptor antagonist famotidine. For example in one patient there was a substantial amelioration of the deficit symptoms of schizophrenia (eg apathy, social withdrawal, and blunted affect) while on famotidine, relapse in these symptoms on withdrawal, and improvement on re-institution of this drug, Kaminski, U.S. Pat. Nos. 5070101 and 5177081. Prell et al (1992) Abstract, part 1, 199.6 Soc. for Neurosci. Annual Meeting, Anaheim Calif. have shown substantially raised levels of N-tele-methyl histamine, a metabolite of histamine in the cerebrospinal fluid of patients with schizophrenia which correlates with those patients with the occurrence of negative symptoms of this disorder assessed using the Psychiatric Symptoms Assessment Scale. These levels were not significantly different between patients free from medication and those on neuroleptic therapy. It is therefore postulated that there is an increase in histaminergic activity in patients with chronic schizophrenia.

The disclosures of all the above mentioned publications are incorporated herein by reference for all purposes.

Additionally, histamine, acting via its receptors, including the $H_2$ receptor, is believed to be critically involved in a number of diseases of organs other than the brain; these include peptic ulceration, allergic reactions, including asthma, immune-mediated disorders, and possibly some tumours.

The histamine $H_2$ receptor is one of many receptors in the body. Compounds used to treat many diseases work by activating a receptor or inhibiting the action if its natural ligand. Variations in receptors amongst the population are known to be caused by allelic variation and this variation, can alter the response of a disease to a drug amongst patients. An example of this would be the response to clozapine, used to treat, schizophrenia associated with allelic variation in the 5-$HT_{2A}$ receptor demonstrated by Arranz el al (1995) Lancet, 346(8970), 281–282.

SUMMARY OF THE INVENTION

The present invention is concerned in one aspect with improvements in the diagnosis and/or treatment of human neurological and psychiatric disorders, and more particularly in the diagnosis and treatment of schizophrenia. In another aspect, the invention is concerned with improvements in the diagnosis and/or treatment of diseases of other systems or organs of the human body.

As a first step to the present invention, the Applicants devised a new oligonucleotide probe to the human $H_2$ receptor mRNA in accordance with the published cDNA sequence available for the gastric parietal cell. Surprisingly, studies using this probe with in-situ hybridization histochemistry on human post-mortem brain tissue produced evidence of a mismatch in the nucleotide sequence for the brain $H_2$ receptor and the sequence for the gastric parietal cell $H_2$ receptor. This discovery was made by recording melt-curve estimations for the optimum hybridization incubation temperature using the method of Davis et al (1986) "Basic Methods in Molecular Biology" page 77 Elsevier Science Publishing Co. It was found that the sequence mismatch is of the order of 10%.

It was apparent, therefore, that there is a hitherto unrecognised allele or subtype of the human histamine $H_2$ receptor gene, which may be specific to the brain.

In a first aspect, the invention provides a sequence for a novel allele of a human histamine $H_2$ receptor gene comprising up to six single base substitutions compared with the cDNA sequence published by Gantz et al (1991) Biochem Biophys Res Comm 178,3,1386–1392 as follows:

| site of change | base change | amino acid alteration |
|---|---|---|
| 398 | T - C | Val - Gly |
| 525 | A - T | Lys - Asn |
| 620 | A - G | Lys - Asp |
| 649 | A - G | Asn - Asp |
| 692 | A - G | Lys - Arg |
| 802 | G - A | Val - Met |

In another aspect, the invention provides a nucleotide sequence coding for a region of a human histamine $H_2$ receptor, comprising one or more of the following base substitutions compared with the published sequence in Gantz et al (1991) supra, and from which the positional notation is taken:

| site of change | base |
|---|---|
| 398 | C |
| 525 | T |
| 620 | G |
| 649 | G |
| 692 | G |
| 802 | A |

The nucleotide sequence of the invention can, for example, comprise the following sequence (as also listed in SEQ ID NO: 1):

5'

CAGCTCGGGTCGCCATCTCTCTGGTCTTAATTTGGGTCATCTCCATTACCCTGTC

CTTTCTGTCTATCCACCTGGGGTGGAACAGCAGGAACGAGACCAGCAAGGGCAAT

CATACCACCTCTAAGTGCAATGTCCAGGTCAATGAAGTGTACGGGCTGGTGGATG

GGCTGGTCACCTTCTACCTCCCGCTACTGATCATGTGCATCACCTACTACCGCAT

CTTCAGGGTCGCCCGGGATCAGGCCAAGAGGATCGATCACATTAGCTCCTGGAAG

GCAGCCACCATCAGGGAGCACAGAGCCACAGTGACACTGGCCGCCGTCATGGGGG

CCTTCATCATCTGCTGGTTTCCCTACTTCACCGCGTTTGTGTACCGTGGGCTGAG

AGGGGATGATGCCATCAATGAGATGTTA 3'

As a specific exemplification, the nucleotide sequence of the invention can comprise the following sequence (as also listed in SEQ ID NO: 2):

5'

CCAATGGCACAGCCTCTTCCTTTTGCCTGGACTCTACCGCATGCAAGATCACCAT

CACCGTGGTCCTTGCGGTCCTCATCCTCATCACCGTTGCTGGCAATGTGGTCGTC

TGTCTGGCCGTGGGCTTGAACCGCCGGCTCCGCAACCTGACCAATTGTTTCATCG

-continued

```
TGTCCTTGGCTATCACTGACCTGCTCCTCGGCCTCCTGGTGCTGCCCTTCTCTGC

CATCTACCAGCTGTCCTGCAAGTGGAGCTTTGGCAAGGTCTTCTGCAATATCTAC

ACCAGCCTGGATGTGATGCTCTGCACAGCCTCCATTCTTAACCTCTTCATGATCA

GCCTCGACCGGTACTGCGCTGTCATGGACCCACTGCGGTACCCTGTGCTGGTCAC

CCCAGCTCGGGTCGCCATCTCTCTGGTCTTAATTTGGGTCATCTCCATTACCCTG

TCCTTTCTGTCTATCCACCTGGGGTGGAACAGCAGGAACGAGACCAGCAAGGGCA

ATCATACCACCTCTAAGTGCAATGTCCAGGTCAATGAAGTGTACGGGCTGGTGGA

TGGGCTGGTCACCTTCTACCTCCCGCTACTGATCATGTGCATCACCTACTACCGC

ATCTTCAGGGTCGCCCGGGATCAGGCCAAGAGGATCGATCACATTAGCTCCTGGA

AGGCAGCCACCATCAGGGAGCACAGAGCCACAGTGACACTGGCCGCCGTCATGGG

GGCCTTCATCATCTGCTGGTTTCCCTACTTCACCGCGTTTGTGTACCGTGGGCTG

AGAGGGGATGATGCCATCAATGAGATGTTAGAAGCCATCGTTCTGTGGCTGGGCT

ATGCCAACTCAGCCCTGAACCCCATCCTGTATGCTGCGCTGAACAGAGACTTCCG

CACCGGGTACCAACAGCTCTTCTGCTGCAGGCTGGCCAACCGCAACTCCCACAAA

ACTTCTCTGAGGTCCAACGCCTCTCAGCTGTCCAGGACCCAAAGCCGAGAACCCA

GGCAACAGGAAGAGAAACCCCTGAAGCTCCAGGTGTGGAGTGGGACAGAAGTCACG
3'
```

In another aspect of the invention, a series of new oligonucleotide primers have been developed for the identification of sequences in a sample comprising a human histamine $H_2$ receptor DNA, cDNA or RNA originating from a tissue sample or body fluid.

In this aspect, the invention provides new oligonucleotides, suitable for use as primers for the amplification of DNA corresponding to a region of a human histamine $H_2$ receptor, having nucleotide sequences selected from:

1) 5' CCAATGGCACAGCCTCTT 3' (as listed in SEQ ID NO: 3)

2) 5' CGTGACTTCTGTCCCACT 3' (as listed in SEQ ID NO: 4)

3) 5' CCAGGCAACAGGAAGAGA 3' (as listed in SEQ ID NO: 5)

4) 5' TCTCTTCCTGTTGCCTGG 3' (as listed in SEQ ID NO: 6)

5) 5' GCAGCAGAAGAGCTGTTG 3' (as listed in SEQ ID NO: 7)

6) 5' TCCAGGTCAATGAAGTGT 3' (as listed in SEQ ID NO: 8)

7) 5' ACACTTCATTGACCTGGA 3' (as listed in SEQ ID NO: 9)

8) 5' CCAAGAGGATCAATCACA 3' (as listed in SEQ ID NO: 10)

9) 5' TGTGATTGATCCTCTTGG 3' (as listed in SEQ ID NO: 11)

and a diagnostic kit comprising one or more of the new oligonucleotides.

The direction and base start numbers for the novel oligonucleotide primers are as follows:

| Primer | Base Start No. |
| --- | --- |
| 1) Upstream | 8 |
| 2) Downstream | 1036 and 1095 |
| 3) Upstream | 995 |
| 4) Downstream | 1012 (no. 3) in reverse) |
| 5) Downstream | 898 and 1171 |
| 6) Upstream | 527 |
| 7) Downstream | 544 (no. 6) in reverse) |
| 8) Upstream | 638 |
| 9) Downstream | 655 (no. 8) in reverse) |

Information on the human histamine $H_2$ receptor was obtained from the MRC Daresbury database accessing "Genem 61" File no. M64799—Human histamine $H_2$ receptor gene.

The above mentioned substitutions alter and in some instances introduce or remove new sites for cleavage by specific restriction endonucleases as follows:

| base change site | alters restriction map of: |
| --- | --- |
| 398 | AluI, AvaI, BspWI, BsrI, CviJI |
| 525 | |
| 620 | Eco57 |
| 649 | ClaI, Sau3A, TaqI |
| 692 | |
| 802 | MnlI |

The invention further provides a diagnostic kit comprising one or more of the new oligonucleotide primers and, preferably, one or more of the above mentioned endonucleases, optionally with one or more buffers.

A kit may be used to establish genotype or base variations. This information may be used in predicting an individuals disease susceptibility, disease course, prognosis and/or response to treatment as would be understood by those skilled in the art from the disclosure contained herein. The treatment response or efficacy which may be predicted may include drug treatment such as for example, use of $H_2$ receptor antagonist like famotidine or other forms of treatment such as social or psychological intervention.

Eucaryotic expression vectors comprising a DNA sequence coding for a protein and or a peptide according to the invention are new materials and are also included in the invention. Host cells, for example, cloned human cell lines, such as NTera 2 c.d1, can be transformed using the new expression vectors and are also included in the invention.

DETAILED DESCRIPTION

Figure 1:
FIG. 1 is a photograph of an agarose gel containing isolated nucleic acids of the invention.

Expression vectors and host cells transformed thereby, in accordance with the invention, can be prepared, for example, as detailed below, and the encoded protein studied, by one or more of the following exemplary methods:

1. Total RNA is extracted from homogenised human tissue, eg. brain, by the acid guanidine thiocyanate method (Chomczynski & Saach (1987), anal. Biochem. 161, 156–159). Messenger RNA (mRNA) is purified from this by hybridisation of oligo(d)T to the polyadenylated tails present on the majority of mRNA's, for example, using the Promega PolyAttract® system. Reverse transcription of the mRNA using specific reverse transcriptase enzyme, eg. Superscipt II, Gibco BRL, is followed by PCR amplification of the resultant product using specific oligonucleotide primers, for example, those previously described. The resulting amplified cDNA is ligated into an expression vector, eg. pGEMEX®-1 vector available from Promega. Competent cells, eg. bacterial strain JM109(DE3), also available from Promega, are transformed using this vector, effective transforms selected and cultured. Expression of the encoded protein is then induced with a suitable promotor, eg. IPTG, and the expressed protein purified from the cell culture using standard biochemical procedures, eg. cell lysis and poly-acrylamide gel electrophoresis.

2. An alternative method for examining the functional protein encoded by the cDNA described above, is to induce transcription of the cloned cDNA, as above, and to purify the specific mRNA from the cell culture as described. The purified mRNA is introduced into competent cells, eg. frog oocytes or Chinese hamster ovary cells, and the function of the encoded protein studied by standard pharmacological and physiological techniques, eg. microelectrode recording and receptor binding techniques.

3. As 1 above, but introducing the cDNA into a coupled transcription-translation system, eg. TNT, Promega with subsequent purification and analysis of the encoded protein as described.

The invention is illustrated by the following Examples:

EXAMPLE 1

This example describes the identification and sequencing of an allelic human $H_2$ receptor gene using certain novel oligonucleotide primers according to the invention.

A polymerase chain reaction (PCR) product is prepared from human DNA.

DNA was extracted from human brain tissue by first pulverizing approximately 1 g of tissue in liquid nitrogen then adding to 10 ml lysis buffer (0.32M sucrose, 10 mM Tris, 5 mM magnesium chloride 1% Triton X-100 pH8.0). This solution was centrifuged (9,000 rpm 15 mins) to pellet the tissue, the lysis buffer was drawn off and the pellet resuspended in 4.5 ml 75 mM sodium chloride, 24 mM EDTA. This solution was then incubated for 3 hours with 250 µl 10% SDS and 2 mg proteinase K at 56° C. This aqueous phase was then extracted twice with 5 ml of phenol:chloroform:isoamyl alcohol (25:24:1). Then sodium acetate to 0.3M pH7.5 and 2 volumes of ethanol (at −20° C.) were added to the aqueous phase and the DNA hooked out into TE buffer. The concentration of the DNA was determined by measuring the optical density of the sample, at a wavelength of 260 nm.

The DNA was then amplified by the polymerase chain reaction using the oligonucleotide primers 1) and 2) (as hereinbefore described) for 36 cycles. The timing for each cycle was as follows; 1 min at 94° C., 1.5 min at 56° C. and 2 mins at 72° C., this was then followed by a 10 min extension at 72° C. (Amplitaq DNA polymerase Perkin-Elmer Cetus). This reaction produced a DNA fragment of 1047 base pair when analyzed by gel electrophoresis.

Following PCR amplification of the DNA, the PCR products were immediately ligated and cloned into the TA cloning system (InvitroGen). The transformed cells were plated onto Luria-Bertani plates containing 50 µl/ml ampicillin and 1.6 mg X-Gal. Plates were then incubated overnight at 37° C., then moved to 4° C. for 4 hours to allow for colour development. Positive (white colonies) were then analyzed by growing a 5 ml culture overnight at 37° C. extracting the plasmids (Qiaspin minipreps (Qiagen)) and performing an EcoRI digest to ensure the correct size product was contained in the plasmid. The plasmid used to clone the PCR product is the pCR™II Vector, which is transformed into One Shot™ INVαF' Competent cells.

Both strands of the cloned PCR product were sequenced using the dideoxynucleotide chain-terminated method, carried out with Sequenase version 2.0 (Amersham/USB). Partial sequencing of short stretches of the cloned DNA utilised all the oligonucleotide primers 1) to 9) hereinbefore described. The cloned PCR product was shown to be identical to the gastric cDNA of Gantz et al except for the previously mentioned six single base changes.

Results and discussions

The sequence derived from the above described method is listed below and in SEQ ID NO: 2.

5'

CCAATGGCACAGCCTCTTCCTTTTGCCTGGACTCTACCGCATGCAAGATCACCAT

CACCGTGGTCCTTGCGGTCCTCATCCTCATCACCGTTGCTGGCAATGTGGTCGTC

TGTCTGGCCGTGGGCTTGAACCGCCGGCTCCGCAACCTGACCAATTGTTTCATCG

TGTCCTTGGCTATCACTGACCTGCTCCTCGGCCTCCTGGTGCTGCCCTTCTCTGC

-continued

```
CATCTACCAGCTGTCCTGCAAGTGGAGCTTTGGCAAGGTCTTCTGCAATATCTAC

ACCAGCCTGGATGTGATGCTCTGCACAGCCTCCATTCTTAACCTCTTCATGATCA

GCCTCGACCGGTACTGCGCTGTCATGGACCCACTGCGGTACCCTGTGCTGGTCAC

CCCAGCTCGGGTCGCCATCTCTCTGGTCTTAATTTGGGTCATCTCCATTACCCTG

TCCTTTCTGTCTATCCACCTGGGGTGGAACAGCAGGAACGAGACCAGCAAGGGCA

ATCATACCACCTCTAAGTGCAATGTCCAGGTCAATGAAGTGTACGGGCTGGTGGA

TGGGCTGGTCACCTTCTACCTCCCGCTACTGATCATGTGCATCACCTACTACCGC

ATCTTCAGGGTCGCCCGGGATCACGCCAAGAGGATCGATCACATTAGCTCCTGGA

AGGCAGCCACCATCAGGGAGCACAGAGCCACAGTGACACTGGCCGCCGTCATGGG

GGCCTTCATCATCTGCTGGTTTCCCTACTTCACCGCGTTTGTGTACCGTGGGCTG

AGAGGGGATGATGCCATCAATGAGATGTTAGAAGCCATCGTTCTGTGGCTGGGCT

ATGCCAACTCAGCCCTGAACCCCATCCTGTATGCTGCGCTGAACAGAGACTTCCG

CACCGGGTACCAACAGCTCTTCTGCTGCAGGCTGGCCAACCGCAACTCCCACAAA

ACTTCTCTGAGGTCCAACGCCTCTCAGCTGTCCAGGACCCAAAGCCGAGAACCCA

GGCAACAGGAAGAGAAACCCCTGAAGCTCCAGGTGTGGAGTGGGACAGAAGTCACG

3'
```

EXAMPLE 2

This example describes the confirmation of the presence of the base changes in a larger population. This is made possible by an assay based upon PCR amplification of a 909 base pair fragment of the $H_2$ receptor gene from human DNA, followed by cleavage utilising specific restriction endonucleases. It will apparent to those skilled in the art that single base changes could be detected using other techniques known to those in the art which include single stranded confirmational polymorphisms (sscp), chemical cleavage, PCR thermoligase reactions etc.

Samples of blood are collected from human volunteers into EDTA coated tube, 1 ml of this blood is heated to 100° C. for 15 minutes then spun in a microcentrifuge at 13,000Xg for 15 minutes. This supernatant is collected, and the cell debris is discarded. Then 0.5–3 µl of this supernatant is utilised as template DNA for a PCR reaction to amplify a portion of the receptor gene between bases 8 and 915. The conditions for this PCR reaction are 3 mM $MgCl_2$ (Gibco BRL),1X PCR buffer (Gibco BRL) 1 mM of each dATP, dGTP, dGTP and dTTP (Promega) 10 pmoles of each of oligonucleotide primers 1) and 5) (hereinbefore described) and 1 unit Taq DNA polymerase (Gibco BRL), in a total volume adjusted to 50 µl by sterile DNAse free water. This mix is then subjected to the following conditions; 96° C. 5 minutes, then 35 cycles of 96° C. for 1 minute, 56° C. for 1 minute, 72° C. for 1 minute and 20 seconds.

10 µl of the resultant products are then analysed on a 1% agarose gel to ensure that the above reaction is correctly amplifying the target DNA fragment. Then 11.5 µl of the PCR mix is added to 2 units Taq1 restriction endonuclease (Fermentas) and 1.5 µl of 10X buffer and incubated at 65° C. for 3–24 hours. The products of this reaction are then analysed on a 2.5% agarose gel. If the original sequence described by Gantz (nominated $H_2A$) has been amplified, then bands of 574 and 335 base pairs are seen which indicates that the individual is an A/A homozygote. If the sequence described in Example 1 (nominated $H_2B$) has been amplified, then following the TaqI cleavage of the PCR product, bands of 335, 306 and 268 base pairs can be seen, indicating that that individual is a B/B homozygote. If bands of 574, 335, 306 and 268 base pairs can be seen, then that individual is an A/B heterozygote.

Typical results are illustrated in FIG. 1, which shows a 2.5% TBE Agarose gel stained with ethidium bromide, showing TαqI digestion patterns of a 909 base pair PCR fragment, from 4 separate individuals.

Lanes A+G - 100 base pair DNA marker (Gibco BRL)

Lanes B+F - Band pattern indicative of an A/B heterozygote

Lanes C+E - Band pattern indicative of an B/B homozygote

Lane D - Blank

Arrows indicated the sizes of the DNA fragments in lanes B to F.

Primers: Oswell DNA Services)

1) upstream: 5' CCAATGGCACAGCCTCTT 3' (as in SEQ ID NO:1)

2) upstream: 5' CCAGGCAACAGGAAGAGA 3' (as in SEQ ID NO:5)

5) downstream: 5' GCAGCAGAAGAGCTGTTG 3' (as in SEQ ID NO:7)

EXAMPLE 3

A method as described in example 2 is applied to a series of DNA samples extracted from schizophrenic individuals, their first degree relatives, and normal controls. There is observed a statistically significant difference of P less than 0.01 the pattern seen in the genotype of these individuals, as described in the table below:

| Diagnosis | H₂ Genotype | | |
|---|---|---|---|
| | A/A | A/B | B/B |
| Controls | 12.1% | 48.5% | 39.4% |
| Schizophrenia | 9.8% | 26.8% | 63.4% |
| 1st degree relatives | 6.1% | 12.1% | 81.8% |

Discussion

The variable sequence is explained by a polymorphic allelic variation within the human population for the gene encoding the H₂ receptor protein. This allelic polymorphism may lead to substantial variation in the effect of activation of the encoded receptor by histamine, either in the efficacy of histamine binding, the duration of activation, or the intracellular effects of such activation. It is envisaged that such variation resulting from allelic polymorphism may underline susceptibility to specific disorders, both affecting the brain and/or involving other systems or organs. In summary, this variation in the human H₂ receptor gene and its products, including, for example, mRNA and proteins, could be used as a method of establishing individual risk to a particular psychiatric or neurological or other illness eg. schizophrenia.

Alternative embodiments of the invention can be envisaged by those skilled in the art from the information contained herein. All such alternative embodiments are intended to lie within the scope of this application.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract and drawings), and/or all of the steps or any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiments. This invention extends to any novel one, or any novel combination, of the features disclosed in this specification (including any accompanying claims, abstract and drawings), or to any novel one, or any novel combination, of the steps of any method or process so disclosed.

We claim:

1. An isolated nucleic acid comprising at least 413 contiguous nucleotides of SEQ ID NO:14, wherein the 413 contiguous nucleotides contain one or more of the mutations selected from the group consisting of T to C at nucleotide 398, A to T at nucleotide 525, A to G at nucleotide 620, A to G at nucleotide 649, A to G at nucleotide 692, and G to A at nucleotide 802, wherein the nucleotide numberings are relative to SEQ ID NO:14.

2. The nucleic acid of claim 1, wherein the nucleic acid comprises SEQ ID NO:1.

3. The nucleic acid of claim 1, wherein the nucleic acid comprises SEQ ID NO:2.

4. An isolated polypeptide encoded by the nucleic acid of claim 1, wherein the polypeptide comprises an amino acid sequence encoded by at least 413 contiguous nucleotides of SEQ ID NO:14.

5. A nucleic acid vector comprising the nucleic acid of claim 1.

6. A nucleic acid primer consisting of a nucleotide sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

7. A method of amplifying or sequencing a nucleic acid, the method comprising hybridizing a target nucleic acid with the nucleic acid primer of claim 6, and extending the nucleic acid primer using the target nucleic acid as a template, wherein the target nucleic acid is suspected of containing an allelic single nucleotide polymorphism.

8. A cell containing the nucleic acid vector of claim 5.

* * * * *

SEQUENCE LISTING

```
<160> NUMBER OF SEQ ID NOS: 15

<210> SEQ ID NO 1
<211> LENGTH: 413
<212> TYPE: DNA
<213> ORGANISM: Homo sapiens
<220> FEATURE:
<221> NAME/KEY: CDS
<222> LOCATION: (3)...(413)

<400> SEQUENCE: 1 ca gct cgg gtc gcc atc tct ctg gtc tta att tgg gtc atc tcc att         47
   Ala Arg Val Ala Ile Ser Leu Val Leu Ile Trp Val Ile Ser Ile
   1               5                   10                  15 acc ctg tcc ttt ctg tct atc cac ctg ggg tgg aac agc agg aac gag         95
Thr Leu Ser Phe Leu Ser Ile His Leu Gly Trp Asn Ser Arg Asn Glu
                20                  25                  30 acc agc aag ggc aat cat acc acc tct aag tgc aat gtc cag gtc aat        143
Thr Ser Lys Gly Asn His Thr Thr Ser Lys Cys Asn Val Gln Val Asn
            35                  40                  45 gaa gtg tac ggg ctg gtg gat ggg ctg gtc acc ttc tac ctc ccg cta        191
Glu Val Tyr Gly Leu Val Asp Gly Leu Val Thr Phe Tyr Leu Pro Leu
        50                  55                  60 ctg atc atg tgc atc acc tac tac cgc atc ttc agg gtc gcc cgg gat        239
Leu Ile Met Cys Ile Thr Tyr Tyr Arg Ile Phe Arg Val Ala Arg Asp
    65                  70                  75 cag gcc aag agg atc gat cac att agc tcc tgg aag gca gcc acc atc        287
Gln Ala Lys Arg Ile Asp His Ile Ser Ser Trp Lys Ala Ala Thr Ile
80                  85                  90                  95 agg gag cac aga gcc aca gtg aca ctg gcc gcc gtc atg ggg gcc ttc        335
Arg Glu His Arg Ala Thr Val Thr Leu Ala Ala Val Met Gly Ala Phe
                100                 105                 110 atc atc tgc tgg ttt ccc tac ttc acc gcg ttt gtg tac cgt ggg ctg        383
```

```
Ile Ile Cys Trp Phe Pro Tyr Phe Thr Ala Phe Val Tyr Arg Gly Leu
        115                 120                 125 aga ggg gat gat gcc atc aat gag atg tta                              413
Arg Gly Asp Asp Ala Ile Asn Glu Met Leu
        130                 135

<210> SEQ ID NO 2
<211> LENGTH: 1046
<212> TYPE: DNA
<213> ORGANISM: Homo sapiens
<220> FEATURE:
<221> NAME/KEY: CDS
<222> LOCATION: (3)...(1046)

<400> SEQUENCE: 2 cc aat ggc aca gcc tct tcc ttt tgc ctg gac tct acc gca tgc aag        47
   Asn Gly Thr Ala Ser Ser Phe Cys Leu Asp Ser Thr Ala Cys Lys
    1               5                  10                  15 atc acc atc acc gtg gtc ctt gcg gtc ctc atc ctc atc acc gtt gct       95
Ile Thr Ile Thr Val Val Leu Ala Val Leu Ile Leu Ile Thr Val Ala
             20                  25                  30 ggc aat gtg gtc gtc tgt ctg gcc gtg ggc ttg aac cgc cgg ctc cgc      143
Gly Asn Val Val Val Cys Leu Ala Val Gly Leu Asn Arg Arg Leu Arg
         35                  40                  45 aac ctg acc aat tgt ttc atc gtg tcc ttg gct atc act gac ctg ctc      191
Asn Leu Thr Asn Cys Phe Ile Val Ser Leu Ala Ile Thr Asp Leu Leu
     50                  55                  60 ctc ggc ctc ctg gtg ctg ccc ttc tct gcc atc tac cag ctg tcc tgc      239
Leu Gly Leu Leu Val Leu Pro Phe Ser Ala Ile Tyr Gln Leu Ser Cys
 65                  70                  75 aag tgg agc ttt ggc aag gtc ttc tgc aat atc tac acc agc ctg gat      287
Lys Trp Ser Phe Gly Lys Val Phe Cys Asn Ile Tyr Thr Ser Leu Asp
 80                  85                  90                  95 gtg atg ctc tgc aca gcc tcc att ctt aac ctc ttc atg atc agc ctc      335
Val Met Leu Cys Thr Ala Ser Ile Leu Asn Leu Phe Met Ile Ser Leu
                 100                 105                 110 gac cgg tac tgc gct gtc atg gac cca ctg cgg tac cct gtg ctg gtc      383
Asp Arg Tyr Cys Ala Val Met Asp Pro Leu Arg Tyr Pro Val Leu Val
             115                 120                 125 acc cca gct cgg gtc gcc atc tct ctg gtc tta att tgg gtc atc tcc      431
Thr Pro Ala Arg Val Ala Ile Ser Leu Val Leu Ile Trp Val Ile Ser
         130                 135                 140 att acc ctg tcc ttt ctg tct atc cac ctg ggg tgg aac agc agg aac      479
Ile Thr Leu Ser Phe Leu Ser Ile His Leu Gly Trp Asn Ser Arg Asn
     145                 150                 155 gag acc agc aag ggc aat cat acc acc tct aag tgc aat gtc cag gtc      527
Glu Thr Ser Lys Gly Asn His Thr Thr Ser Lys Cys Asn Val Gln Val
160                 165                 170                 175 aat gaa gtg tac ggg ctg gtg gat ggg ctg gtc acc ttc tac ctc ccg      575
Asn Glu Val Tyr Gly Leu Val Asp Gly Leu Val Thr Phe Tyr Leu Pro
                 180                 185                 190 cta ctg atc atg tgc atc acc tac tac cgc atc ttc agg gtc gcc cgg      623
Leu Leu Ile Met Cys Ile Thr Tyr Tyr Arg Ile Phe Arg Val Ala Arg
             195                 200                 205 gat cag gcc aag agg atc gat cac att agc tcc tgg aag gca gcc acc      671
Asp Gln Ala Lys Arg Ile Asp His Ile Ser Ser Trp Lys Ala Ala Thr
         210                 215                 220 atc agg gag cac aga gcc aca gtg aca ctg gcc gcc gtc atg ggg gcc      719
Ile Arg Glu His Arg Ala Thr Val Thr Leu Ala Ala Val Met Gly Ala
     225                 230                 235 ttc atc atc tgc tgg ttt ccc tac ttc acc gcg ttt gtg tac cgt ggg      767
Phe Ile Ile Cys Trp Phe Pro Tyr Phe Thr Ala Phe Val Tyr Arg Gly
```

-continued

```
              240                 245                 250                 255
ctg aga ggg gat gat gcc atc aat gag atg tta gaa gcc atc gtt ctg         815
Leu Arg Gly Asp Asp Ala Ile Asn Glu Met Leu Glu Ala Ile Val Leu
            260                 265                 270 tgg ctg ggc tat gcc aac tca gcc ctg aac ccc atc ctg tat gct gcg         863
Trp Leu Gly Tyr Ala Asn Ser Ala Leu Asn Pro Ile Leu Tyr Ala Ala
            275                 280                 285 ctg aac aga gac ttc cgc acc ggg tac caa cag ctc ttc tgc tgc agg         911
Leu Asn Arg Asp Phe Arg Thr Gly Tyr Gln Gln Leu Phe Cys Cys Arg
            290                 295                 300 ctg gcc aac cgc aac tcc cac aaa act tct ctg agg tcc aac gcc tct         959
Leu Ala Asn Arg Asn Ser His Lys Thr Ser Leu Arg Ser Asn Ala Ser
            305                 310                 315 cag ctg tcc agg acc caa agc cga gaa ccc agg caa cag gaa gag aaa        1007
Gln Leu Ser Arg Thr Gln Ser Arg Glu Pro Arg Gln Gln Glu Glu Lys
320                 325                 330                 335 ccc ctg aag ctc cag gtg tgg agt ggg aca gaa gtc acg                    1046
Pro Leu Lys Leu Gln Val Trp Ser Gly Thr Glu Val Thr
                340                 345
```

<210> SEQ ID NO 3
<211> LENGTH: 18
<212> TYPE: DNA
<213> ORGANISM: Artificial sequence
<220> FEATURE:
<221> NAME/KEY: Synthetic Oligonucleotide

<400> SEQUENCE: 3
ccaatggcac agcctctt                                                      18

<210> SEQ ID NO 4
<211> LENGTH: 18
<212> TYPE: DNA
<213> ORGANISM: Artificial sequence
<220> FEATURE:
<221> NAME/KEY: Synthetic Oligonucleotide

<400> SEQUENCE: 4
cgtgacttct gtcccact                                                      18

<210> SEQ ID NO 5
<211> LENGTH: 18
<212> TYPE: DNA
<213> ORGANISM: Artificial sequence
<220> FEATURE:
<221> NAME/KEY: Synthetic Oligonucleotide

<400> SEQUENCE: 5
ccaggcaaca ggaagaga                                                      18

<210> SEQ ID NO 6
<211> LENGTH: 18
<212> TYPE: DNA
<213> ORGANISM: Artificial sequence
<220> FEATURE:
<221> NAME/KEY: Synthetic Oligonucleotide

<400> SEQUENCE: 6
tctcttcctg ttgcctgg                                                      18

<210> SEQ ID NO 7
<211> LENGTH: 18
<212> TYPE: DNA
<213> ORGANISM: Artificial sequence
<220> FEATURE:

-continued

<221> NAME/KEY: Synthetic Oligonucleotide

<400> SEQUENCE: 7
gcagcagaag agctgttg                                            18

<210> SEQ ID NO 8
<211> LENGTH: 18
<212> TYPE: DNA
<213> ORGANISM: Artificial sequence
<220> FEATURE:
<221> NAME/KEY: Synthetic Oligonucleotide

<400> SEQUENCE: 8
tccaggtcaa tgaagtgt                                            18

<210> SEQ ID NO 9
<211> LENGTH: 18
<212> TYPE: DNA
<213> ORGANISM: Artificial sequence
<220> FEATURE:
<221> NAME/KEY: Synthetic Oligonucleotide

<400> SEQUENCE: 9
acacttcatt gacctgga                                            18

<210> SEQ ID NO 10
<211> LENGTH: 18
<212> TYPE: DNA
<213> ORGANISM: Artificial sequence
<220> FEATURE:
<221> NAME/KEY: Synthetic Oligonucleotide

<400> SEQUENCE: 10
ccaagaggat caatcaca                                            18

<210> SEQ ID NO 11
<211> LENGTH: 18
<212> TYPE: DNA
<213> ORGANISM: Artificial sequence
<220> FEATURE:
<221> NAME/KEY: Synthetic Oligonucleotide

<400> SEQUENCE: 11
tgtgattgat cctcttgg                                            18

<210> SEQ ID NO 12
<211> LENGTH: 137
<212> TYPE: PRT
<213> ORGANISM: Homo sapiens

<400> SEQUENCE: 12

Ala Arg Val Ala Ile Ser Leu Val Leu Ile Trp Val Ile Ser Ile Thr
 1               5                  10                  15

Leu Ser Phe Leu Ser Ile His Leu Gly Trp Asn Ser Arg Asn Glu Thr
                20                  25                  30

Ser Lys Gly Asn His Thr Thr Ser Lys Cys Asn Val Gln Val Asn Glu
            35                  40                  45

Val Tyr Gly Leu Val Asp Gly Leu Val Thr Phe Tyr Leu Pro Leu Leu
        50                  55                  60

Ile Met Cys Ile Thr Tyr Tyr Arg Ile Phe Arg Val Ala Arg Asp Gln
65                  70                  75                  80

Ala Lys Arg Ile Asp His Ile Ser Ser Trp Lys Ala Ala Thr Ile Arg
                85                  90                  95

```
Glu His Arg Ala Thr Val Thr Leu Ala Ala Val Met Gly Ala Phe Ile
            100                 105                 110

Ile Cys Trp Phe Pro Tyr Phe Thr Ala Phe Val Tyr Arg Gly Leu Arg
        115                 120                 125

Gly Asp Asp Ala Ile Asn Glu Met Leu
    130                 135

<210> SEQ ID NO 13
<211> LENGTH: 348
<212> TYPE: PRT
<213> ORGANISM: Homo sapiens

<400> SEQUENCE: 13

Asn Gly Thr Ala Ser Ser Phe Cys Leu Asp Ser Thr Ala Cys Lys Ile
  1               5                  10                  15

Thr Ile Thr Val Val Leu Ala Val Leu Ile Leu Thr Val Ala Gly
             20                  25                  30

Asn Val Val Cys Leu Ala Val Gly Leu Asn Arg Arg Leu Arg Asn
             35                  40                  45

Leu Thr Asn Cys Phe Ile Val Ser Leu Ala Ile Thr Asp Leu Leu Leu
     50                  55                  60

Gly Leu Leu Val Leu Pro Phe Ser Ala Ile Tyr Gln Leu Ser Cys Lys
 65                  70                  75                  80

Trp Ser Phe Gly Lys Val Phe Cys Asn Ile Tyr Thr Ser Leu Asp Val
                 85                  90                  95

Met Leu Cys Thr Ala Ser Ile Leu Asn Leu Phe Met Ile Ser Leu Asp
            100                 105                 110

Arg Tyr Cys Ala Val Met Asp Pro Leu Arg Tyr Pro Val Leu Val Thr
            115                 120                 125

Pro Ala Arg Val Ala Ile Ser Leu Val Leu Ile Trp Val Ile Ser Ile
    130                 135                 140

Thr Leu Ser Phe Leu Ser Ile His Leu Gly Trp Asn Ser Arg Asn Glu
145                 150                 155                 160

Thr Ser Lys Gly Asn His Thr Thr Ser Lys Cys Asn Val Gln Val Asn
                165                 170                 175

Glu Val Tyr Gly Leu Val Asp Gly Leu Val Thr Phe Tyr Leu Pro Leu
            180                 185                 190

Leu Ile Met Cys Ile Thr Tyr Tyr Arg Ile Phe Arg Val Ala Arg Asp
            195                 200                 205

Gln Ala Lys Arg Ile Asp His Ile Ser Ser Trp Lys Ala Ala Thr Ile
    210                 215                 220

Arg Glu His Arg Ala Thr Val Thr Leu Ala Ala Val Met Gly Ala Phe
225                 230                 235                 240

Ile Ile Cys Trp Phe Pro Tyr Phe Thr Ala Phe Val Tyr Arg Gly Leu
                245                 250                 255

Arg Gly Asp Asp Ala Ile Asn Glu Met Leu Glu Ala Ile Val Leu Trp
            260                 265                 270

Leu Gly Tyr Ala Asn Ser Ala Leu Asn Pro Ile Leu Tyr Ala Ala Leu
            275                 280                 285

Asn Arg Asp Phe Arg Thr Gly Tyr Gln Gln Leu Phe Cys Cys Arg Leu
    290                 295                 300

Ala Asn Arg Asn Ser His Lys Thr Ser Leu Arg Ser Asn Ala Ser Gln
305                 310                 315                 320

Leu Ser Arg Thr Gln Ser Arg Glu Pro Arg Gln Glu Glu Lys Pro
            325                 330                 335
```

-continued

```
Leu Lys Leu Gln Val Trp Ser Gly Thr Glu Val Thr
        340                 345
```

<210> SEQ ID NO 14
<211> LENGTH: 1080
<212> TYPE: DNA
<213> ORGANISM: Homo sapiens
<220> FEATURE:
<221> NAME/KEY: CDS
<222> LOCATION: (1)...(1077)

<400> SEQUENCE: 14

```
atg gca ccc aat ggc aca gcc tct tcc ttt tgc ctg gac tct acc gca        48
Met Ala Pro Asn Gly Thr Ala Ser Ser Phe Cys Leu Asp Ser Thr Ala
 1               5                  10                  15 tgc aag atc acc atc acc gtg gtc ctt gcg gtc ctc atc ctc atc acc        96
Cys Lys Ile Thr Ile Thr Val Val Leu Ala Val Leu Ile Leu Ile Thr
                20                  25                  30 gtt gct ggc aat gtg gtc gtc tgt ctg gcc gtg ggc ttg aac cgc cgg       144
Val Ala Gly Asn Val Val Val Cys Leu Ala Val Gly Leu Asn Arg Arg
            35                  40                  45 ctc cgc aac ctg acc aat tgt ttc atc gtg tcc ttg gct atc act gac       192
Leu Arg Asn Leu Thr Asn Cys Phe Ile Val Ser Leu Ala Ile Thr Asp
        50                  55                  60 ctg ctc ctc ggc ctc ctg gtg ctg ccc ttc tct gcc atc tac cag ctg       240
Leu Leu Leu Gly Leu Leu Val Leu Pro Phe Ser Ala Ile Tyr Gln Leu
 65                  70                  75                  80 tcc tgc aag tgg agc ttt ggc aag gtc ttc tgc aat atc tac acc agc       288
Ser Cys Lys Trp Ser Phe Gly Lys Val Phe Cys Asn Ile Tyr Thr Ser
                85                  90                  95 ctg gat gtg atg ctc tgc aca gcc tcc att ctt aac ctc ttc atg atc       336
Leu Asp Val Met Leu Cys Thr Ala Ser Ile Leu Asn Leu Phe Met Ile
            100                 105                 110 agc ctc gac cgg tac tgc gct gtc atg gac cca ctg cgg tac cct gtg       384
Ser Leu Asp Arg Tyr Cys Ala Val Met Asp Pro Leu Arg Tyr Pro Val
        115                 120                 125 ctg gtc acc cca gtt cgg gtc gcc atc tct ctg gtc ata att tgg gtc       432
Leu Val Thr Pro Val Arg Val Ala Ile Ser Leu Val Ile Ile Trp Val
    130                 135                 140 atc tcc att acc ctg tcc ttt ctg tct atc cac ctg ggg tgg aac agc       480
Ile Ser Ile Thr Leu Ser Phe Leu Ser Ile His Leu Gly Trp Asn Ser
145                 150                 155                 160 agg aac gag acc agc aag ggc aat cat acc acc tct aag tgc aaa gtc       528
Arg Asn Glu Thr Ser Lys Gly Asn His Thr Thr Ser Lys Cys Lys Val
                165                 170                 175 cag gtc aat gaa gtg tac ggg ctg gtg gat ggg ctg gtc acc ttc tac       576
Gln Val Asn Glu Val Tyr Gly Leu Val Asp Gly Leu Val Thr Phe Tyr
            180                 185                 190 ctc ccg cta ctg atc atg tgc atc acc tac tac cgc atc ttc aag gtc       624
Leu Pro Leu Leu Ile Met Cys Ile Thr Tyr Tyr Arg Ile Phe Lys Val
        195                 200                 205 gcc cgg gat cag gcc aag agg atc aat cac att agc tcc tgg aag gca       672
Ala Arg Asp Gln Ala Lys Arg Ile Asn His Ile Ser Ser Trp Lys Ala
    210                 215                 220 gcc acc atc agg gag cac aaa gcc aca gtg aca ctg gcc gcc gtc atg       720
Ala Thr Ile Arg Glu His Lys Ala Thr Val Thr Leu Ala Ala Val Met
225                 230                 235                 240 ggg gcc ttc atc atc tgc tgg ttt ccc tac ttc acc gcg ttt gtg tac       768
Gly Ala Phe Ile Ile Cys Trp Phe Pro Tyr Phe Thr Ala Phe Val Tyr
                245                 250                 255 cgt ggg ctg aga ggg gat gat gcc atc aat gag gtg tta gaa gcc atc       816
Arg Gly Leu Arg Gly Asp Asp Ala Ile Asn Glu Val Leu Glu Ala Ile
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     |     | 260 |     |     |     |     | 265 |     |     |     |     | 270 |      |
| gtt | ctg | tgg | ctg | ggc | tat | gcc | aac | tca | gcc | ctg | aac | ccc | atc | ctg | tat | 864  |
| Val | Leu | Trp | Leu | Gly | Tyr | Ala | Asn | Ser | Ala | Leu | Asn | Pro | Ile | Leu | Tyr |      |
|     |     | 275 |     |     |     |     | 280 |     |     |     |     | 285 |     |     |     |      |
| gct | gcg | ctg | aac | aga | gac | ttc | cgc | acc | ggg | tac | caa | cag | ctc | ttc | tgc | 912  |
| Ala | Ala | Leu | Asn | Arg | Asp | Phe | Arg | Thr | Gly | Tyr | Gln | Gln | Leu | Phe | Cys |      |
|     | 290 |     |     |     |     | 295 |     |     |     |     | 300 |     |     |     |     |      |
| tgc | agg | ctg | gcc | aac | cgc | aac | tcc | cac | aaa | act | tct | ctg | agg | tcc | aac | 960  |
| Cys | Arg | Leu | Ala | Asn | Arg | Asn | Ser | His | Lys | Thr | Ser | Leu | Arg | Ser | Asn |      |
| 305 |     |     |     |     | 310 |     |     |     |     | 315 |     |     |     |     | 320 |      |
| gcc | tct | cag | ctg | tcc | agg | acc | caa | agc | cga | gaa | ccc | agg | caa | cag | gaa | 1008 |
| Ala | Ser | Gln | Leu | Ser | Arg | Thr | Gln | Ser | Arg | Glu | Pro | Arg | Gln | Gln | Glu |      |
|     |     |     |     | 325 |     |     |     |     | 330 |     |     |     |     | 335 |     |      |
| gag | aaa | ccc | ctg | aag | ctc | cag | gtg | tgg | agt | ggg | aca | gaa | gtc | acg | gcc | 1056 |
| Glu | Lys | Pro | Leu | Lys | Leu | Gln | Val | Trp | Ser | Gly | Thr | Glu | Val | Thr | Ala |      |
|     |     |     | 340 |     |     |     |     | 345 |     |     |     |     | 350 |     |     |      |
| ccc | cag | gga | gcc | aca | gac | agg | taa |     |     |     |     |     |     |     |     | 1080 |
| Pro | Gln | Gly | Ala | Thr | Asp | Arg |     |     |     |     |     |     |     |     |     |      |
|     | 355 |     |     |     |     |     |     |     |     |     |     |     |     |     |     |      |

<210> SEQ ID NO 15
<211> LENGTH: 359
<212> TYPE: PRT
<213> ORGANISM: Homo sapiens

<400> SEQUENCE: 15

```
Met Ala Pro Asn Gly Thr Ala Ser Ser Phe Cys Leu Asp Ser Thr Ala
  1               5                  10                  15

Cys Lys Ile Thr Ile Thr Val Val Leu Ala Val Leu Ile Leu Ile Thr
                 20                  25                  30

Val Ala Gly Asn Val Val Val Cys Leu Ala Val Gly Leu Asn Arg Arg
             35                  40                  45

Leu Arg Asn Leu Thr Asn Cys Phe Ile Val Ser Leu Ala Ile Thr Asp
         50                  55                  60

Leu Leu Leu Gly Leu Leu Val Leu Pro Phe Ser Ala Ile Tyr Gln Leu
 65                  70                  75                  80

Ser Cys Lys Trp Ser Phe Gly Lys Val Phe Cys Asn Ile Tyr Thr Ser
                 85                  90                  95

Leu Asp Val Met Leu Cys Thr Ala Ser Ile Leu Asn Leu Phe Met Ile
                100                 105                 110

Ser Leu Asp Arg Tyr Cys Ala Val Met Asp Pro Leu Arg Tyr Pro Val
            115                 120                 125

Leu Val Thr Pro Val Arg Val Ala Ile Ser Leu Val Ile Ile Trp Val
        130                 135                 140

Ile Ser Ile Thr Leu Ser Phe Leu Ser Ile His Leu Gly Trp Asn Ser
145                 150                 155                 160

Arg Asn Glu Thr Ser Lys Gly Asn His Thr Thr Ser Lys Cys Lys Val
                165                 170                 175

Gln Val Asn Glu Val Tyr Gly Leu Val Asp Gly Leu Val Thr Phe Tyr
            180                 185                 190

Leu Pro Leu Leu Ile Met Cys Ile Thr Tyr Tyr Arg Ile Phe Lys Val
        195                 200                 205

Ala Arg Asp Gln Ala Lys Arg Ile Asn His Ile Ser Ser Trp Lys Ala
    210                 215                 220

Ala Thr Ile Arg Glu His Lys Ala Thr Val Thr Leu Ala Ala Val Met
225                 230                 235                 240

Gly Ala Phe Ile Ile Cys Trp Phe Pro Tyr Phe Thr Ala Phe Val Tyr
```

-continued

```
                245                      250                       255

Arg Gly Leu Arg Gly Asp Asp Ala Ile Asn Glu Val Leu Glu Ala Ile
            260                 265                 270

Val Leu Trp Leu Gly Tyr Ala Asn Ser Ala Leu Asn Pro Ile Leu Tyr
            275                 280                 285

Ala Ala Leu Asn Arg Asp Phe Arg Thr Gly Tyr Gln Gln Leu Phe Cys
        290                 295                 300

Cys Arg Leu Ala Asn Arg Asn Ser His Lys Thr Ser Leu Arg Ser Asn
305                 310                 315                 320

Ala Ser Gln Leu Ser Arg Thr Gln Ser Arg Glu Pro Arg Gln Gln Glu
            325                 330                 335

Glu Lys Pro Leu Lys Leu Gln Val Trp Ser Gly Thr Glu Val Thr Ala
            340                 345                 350

Pro Gln Gly Ala Thr Asp Arg
        355
```